Figure 2:
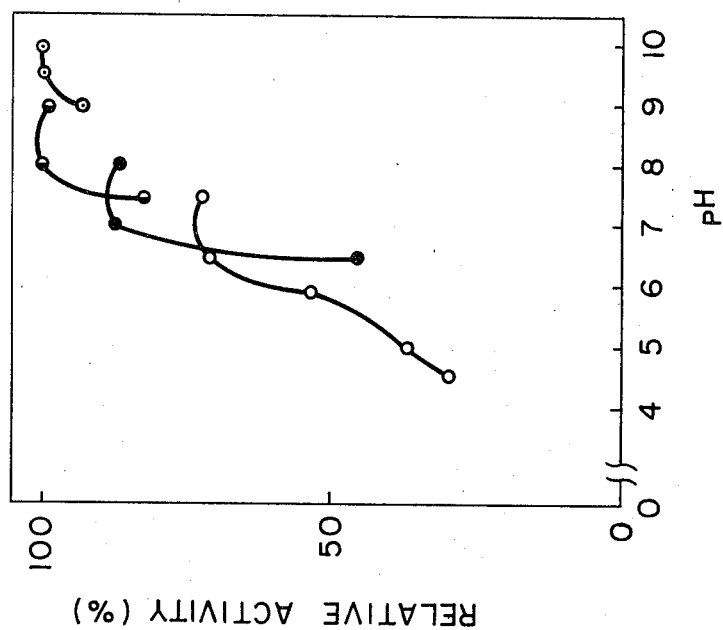

United States Patent [19]

Yoshino et al.

[11] 4,357,425

[45] Nov. 2, 1982

[54] PROCESS FOR PRODUCING L-AMINO ACID OXIDASE

[75] Inventors: Eiichi Yoshino; Hidehiko Ishikawa; Fumitaka Inoue; Masaki Takada; Hideo Misaki, all of Shizuoka, Japan

[73] Assignee: Toyo Jozo Company, Ltd., Tokyo, Japan

[21] Appl. No.: 256,901

[22] Filed: Apr. 23, 1981

[30] Foreign Application Priority Data

Apr. 30, 1980 [JP] Japan ................................. 55-057180

[51] Int. Cl.$^3$ .......................... C12N 9/06; C12R 1/645
[52] U.S. Cl. ..................................... 435/191; 435/911
[58] Field of Search .......................................... 435/191

[56] References Cited

U.S. PATENT DOCUMENTS 4,234,691 11/1980 Kusakabe et al. .................. 435/191

OTHER PUBLICATIONS

Chen et al., in Archives of Biochemistry and Biophysics, vol. 146, pp. 54–63, (1971).
Duerre et al., in Journal of Bacteriology, vol. 121, pp. 656–663, (1975).

Primary Examiner—Lionel M. Shapiro
Attorney, Agent, or Firm—Wyatt, Gerber, Shoup, Scobey & Badie

[57] ABSTRACT

L-amino acid oxidase is obtained by culturing a microorganism which can produce L-amino acid oxidase and belongs to the genus Colletotrichum, e.g. Colletotrichum sp. M5073, deposition number FERMP 5441, in a culturing medium and recovering the oxidase from cells of the microorganism.

2 Claims, 4 Drawing Figures

PROCESS FOR PRODUCING L-AMINO ACID OXIDASE

The present invention relates to a process for producing L-amino acid oxidase.

L-amino acid oxidase is an enzyme with the classification No. EC 1.4.3.2., L-amino acid: oxygen oxidoreductase (deaminating), which operates as shown in the following reaction:

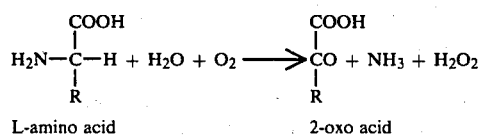

L-amino acid → 2-oxo acid $$H_2N-\underset{R}{\underset{|}{C}}H + H_2O + O_2 \longrightarrow \underset{R}{\underset{|}{C}}O + NH_3 + H_2O_2$$

It has hitherto been known that this enzyme is found in snake venum, the kidneys of rats and mice, the livers of birds, invertebrate animals and *Neurospora crassa* [Arch. Biochem. Biophys., 146, pp. 54–63 (1971); J. Bacteriol., 121, pp. 656–663 (1975), Protein, Nucleic Acid, Enzyme, Vol. 17, pp. 42–55 (1972)].

It has now been found that L-amino acid oxidase can be produced in the mycelium of a mold of M5073, isolated from seeds of *Calophyllum inophyllum* in Hahajima, Bonin Islands, Tokyo, Japan, and have isolated the said enzyme therefrom.

In the accompanying drawings, FIGS. 1–4 show optimum pH, pH stability, heat stability and optimum temperature of the L-amino acid oxidase of this invention.

Observation of the above mold M5073 on various culture media with the naked eyes and under a microscope reveals the following characteristics:

A. Growth on various culture media

1. Malt-extract agar medium

Very fast growth, covering the whole surface of a Petri dish (85 mm in inner diameter) in 5 days when incubated at 26° C. Aerial hyphae downy white during the initial period of the incubation but turn to putty (near grays 1 dc) as the microorganism grows. Clear exudations on colonies. The reverse are basically apricot (hue 4 ga) and partly covert brown (hue 2 nl).

2. Potato-glucose agar medium

Very fast growth, occupying the whole surface of a Petri dish (85 mm in inner diameter) in 5 days when incubated at 26° C. Aerial hyphae downy, white during the initial period of the incubation, but turn to griege (near grays 1 fe) or olive gray (near gray 1 ih). Clear exudations slightly exude on colonies. The reverse are basically pearl pink (hue 3 ca), and partly fog blue (hue 14 ig).

3. Czapeck agar medium

Fast growth, reaching 75–80 mm in diameter in 7 days when incubated at 26° C. Aerial hyphae downy, and the hyphae rise relatively thick. White during the initial period of the incubation, but gradually turns to olive gray (near gray 1 ih) changing from the central part toward the peripheral part as the microorganisms grows. The reverse are flesh pink (hue 4 ca), partly chocolate (hue 4 nl).

The above color descriptions are in accordance with the color descriptive method described in Color Harmony Manual (container Corporation of America 1958).

B. Physiological characteristics

1. Optimum growth conditions

Optimum pH: pH 4–8
Optimum temperature: 24°–30° C.

2. Tolerable growth conditions pH at which the microorganisms can grow: pH 2.5–11 Temperature at which the microorganisms can grow: 8°–42° C.

C. Morphological characteristics

Acervuli brown, plate- or cushion-shape, scattered on the medium. Several brown setae on the edge of the acervuli or between conidiophores. The conidiophores stretch straight from simple and well grown stromata. Colorless, smooth wall surface, with 1–2 segments. $10-60\times3-4\mu$.

The setae are dark brown or dark olive, $50-150\mu$ in length, and $5-7\mu$ in width at the basis, having a smooth wall surface with one to several segments. The conidia are single celled, $10-20\times3-5\mu$, oval and slightly pointed at the basis. The wall surface are smooth and the conidia are formed in a lump at the end of the conidiophores. Mucus and orange. Each individual conidia are colorless or pale yellowish green.

The mold M5073 is identified as belonging to the genus Colletotrichum, on the basis of these characteristics, particularly that the mold M5073 forms dark brown colonies, acervuli with setae well developed, and the conidia are formed in a lump at the end of the simple and well developed conidiophores. The species has not yet been identified, because a microorganism of the genus, Colletotrichum is parasitic on plant and identification of species on the basis of culture is difficult (von Arx, J. A., The Genera of Fungi Sporulating Pure Calture, pp. 315, 1974; J. Cramer, Barron, G. L., The Genera of Hyphomycetes from soil, pp. 364, 1968, The Williams & Wilkins Co.; Tiffany, L. H. and J. C. Gilman, Species of Colletotrichum from Legumes, Mycologia 46: 52–75, 1954).

Based on the above results, the mold M5073 has been named as Colletotrichum sp. M5073 and deposited at Fermentation Research Institute, Agent of Industrial Science and Technology, Japan, under the deposition No. FERM-P No. 5441.

This invention provides a process for producing L-amino acid oxidase by culturing a microorganism of the genus Colletotrichum which is capable of producing L-amino acid oxidase in a suitable culturing medium, and recovering the resulting L-amino acid oxidase from the cultured cells.

Microorganisms useful in the present invention include any one which belong to the genus Colletotrichum and is capable of producing L-amino acid oxidase. Colletotrichum sp. M5073 above is one example. As is known, microorganisms are likely to mutate artificially or naturally. The microorganisms usable in the present invention are, of course, no exception to this rule. Any variant may be used in the present invention as long as it has the ability to produce an L-amino acid oxidase.

In the present process, the microorganism is initially cultured in a culturing medium in a conventional manner. The culturing may be effected on solid or in liquid, but it is advantageous from a commercial point of view to culture the microorganism in a commercial culturing medium with stirring and aeration.

Nutritive sources of the medium may be those conventionally used for the culturing of microorganisms. A carbon source may be any assimilable carbon compound, for example, rice, rice bran, starch, glucose, maltose, glycerin, molasses, soluble starch and the like. A nitrogen source may be any assimilable nitrogen compound, for example, peptone, soy bean powder, corn steep liquor, meat extract, yeast extract, amino acids, nitrates, ammonium sulfate, ammonium chloride and the like. Salts such as sodium chloride, potassium chloride, magnesium sulfate, potassium phosphate monobasic, potassium phosphate dibasic and the like may also be used as required.

The culturing temperature may be varied within the temperature range at which the microorganisms grows to produce L-amino acid oxidase, but preferably 20°–35° C. The culture growth period may also vary depending upon the culturing conditions, but it is usually 2–4 days. Normally growth is continued until the activity of the L-amino acid oxidase reaches its highest level. In culture broth obtained, the L-amino acid oxidase is contained and accumulated in mycelium.

L-amino acid oxidase can be obtained, for example, with the following procedures:

At first, the broth is separated into a solid part and a liquid part, and the wet cells thus obtained are suspended in a Tris-HCl buffer or phosphate buffer solution, if necessary. Then, L-amino acid oxidase is extracted from the cells by applying adequately selected and, if necessary, combined cell-treating methods such as lysozyme treatment, supersonic wave treatment, French Press treatment and the like, whereby a crude liquid containing L-amino acid oxidase is obtained.

The crude liquid is then subjected to a purification process, wherein the crude liquid is treated with known isolation and/or purification procedures for proteins or enzymes to give refined L-amino acid oxidase. For instance, crude L-amino acid oxidase can be recovered from the crude liquid containing L-amino acid oxidase by adding ammonium sulfate to the liquid in order to salt out L-amino acid oxidase. Alternatively, organic solvents such as acetone, ethanol, isopropanol or the like are added in order to precipitate L-amino acid oxidase.

Furthermore, the crude product can be refined to such an extent that, for example, a homogeneous protein thereof is obtained by electrophoresis, taking advantage of properties of L-amino acid oxidase. For instance, the crude L-amino acid oxidase is dissolved in a suitable medium such as a Tris-HCl buffer solution, treated with ion-exchangers such as diethylaminoethyl cellulose (hereinafter "DEAE-cellulose"), cross-linked diethylaminoethyl dextran gel and the like, and gel-filters such as dextran gel, polyacrylamide gel and the like and then, if necessary, concentrated with dialysis membranes, hollow fibers, ultrafiltration membranes and so forth. The refined product thus obtained is then dried by a suitable method such as lypohilization to give refined powders of L-amino acid oxidase.

The L-amino acid oxidase provided by the present invention has the following physical properties. Reference is first made to determination methods for its activity or potency.

(1) Measurement of enzyme activity 0.9 ml of a reaction solution of the following composition is placed in a small test tube and warmed to 37° C.

| | |
|---|---|
| 0.2M L-Leucine | 0.1 ml |
| 0.2M Tris—HCl buffer (pH 7.5) | 0.2 ml |
| 0.3% 4-Aminoantipyrin | 0.1 ml |
| 0.2% Phenol | 0.1 ml |
| Peroxidase (50 U/ml) | 0.1 ml |
| Water | 0.3 ml |

0.1 ml of a liquid containing L-amino acid oxidase is added thereto and reaction continued for exactly for 10 minutes at 37° C. The reaction was terminated by adding 2.0 ml of ethanol. Then, the amount of hydrogen peroxide formed is colorimetrically determined from absorbance measured at 480 nm. The enzymatic activity is determined from the amount of the hydrogen peroxide formed with the following equation:

$$U/ml = \Delta A 480 \text{ nm} \times 0.699 \times \text{dilution rate}$$

The amount of the enzyme which produces $1\mu$ mole of hydrogen peroxide at 37° C. in one minute is defined as one unit (1 U).

(2) Action

In the presence of oxygen, L-amino acid oxidase catalyzes reactions wherein the α-amino group of L-amino acid is oxidatively deaminated to form α-keto acid, ammonia and hydrogen peroxide.

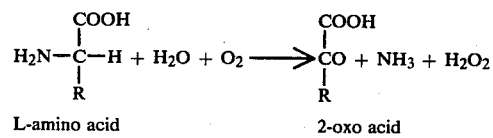

L-amino acid → 2-oxo acid (3) Optimum pH

Figure 1:
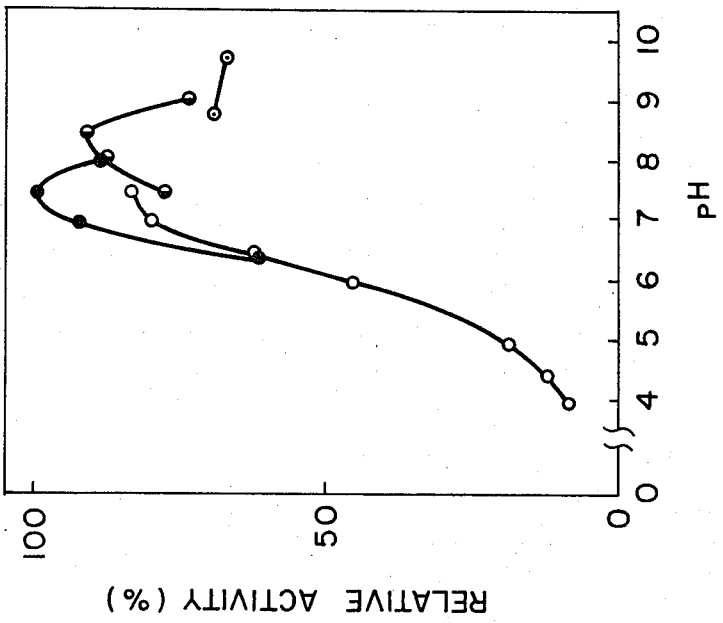

The enzymatic activity of the L-amino acid oxidase is measured at several pH values using a dimethylglutaric acid-NaOH buffer solution (pH 4–7.5), a phosphate buffer solution. (pH 6.5–8.0), a Tris-HCl buffer solution (pH 7.5–9.0) and a glycine-NaOH buffer solution (pH 8.8–9.6). The results are shown in FIG. 1 below, which shows that the optimum pH is pH 7.0–8.5.

(4) pH stability

After the enzyme is kept in a dimethylglutaric acid-NaOH buffer solution (pH 4.5–7.5), a phosphate buffer solution (pH 6.5–8), a Tris-HCl buffer solution (pH 7.5–9) or glycine-NaOH buffer solution (pH 9–10) at 37° C. for 24 hours, its enzymatic activity is measured. The results are as shown in FIG. 2, which shows that it is stable at pH 8 or higher.

(5) Heat-stability

Figure 3:
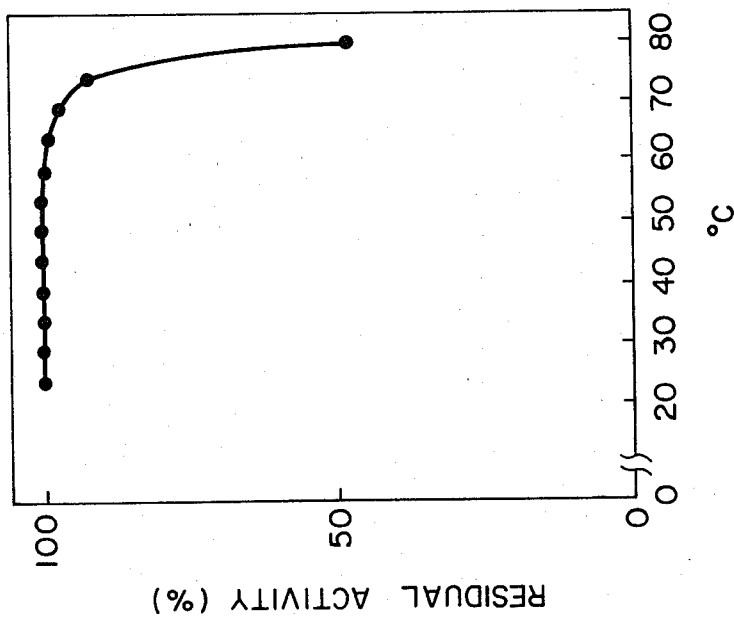

The heat stability of the enzyme is measured by keeping the enzyme in a Tris-HCl buffer solution (pH 7.5) for 10 minutes. Results are shown in FIG. 3. The enzyme is considered stable at 60° C. or lower.

(6) Optimum temperature

Figure 4:
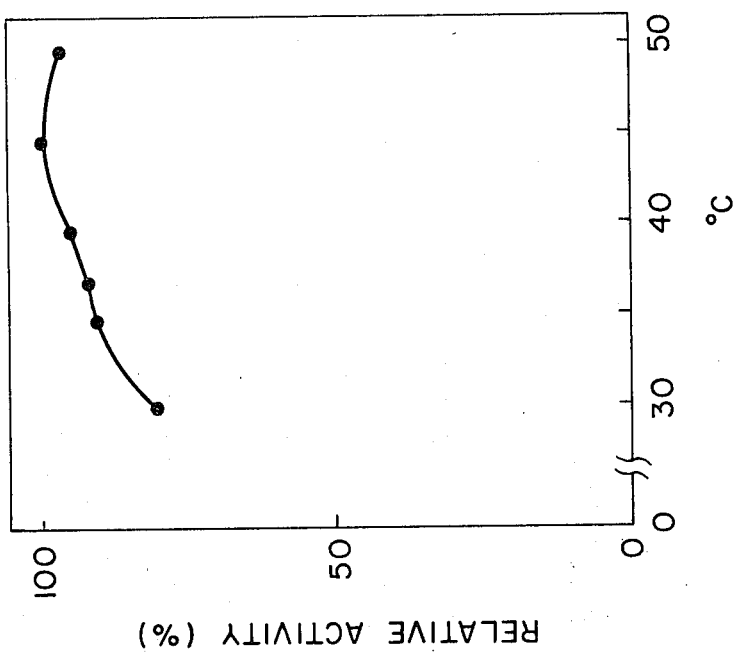

The optimum temperature is measured, using the same reaction solution as the one used for the measurement of the enzyme activity. Results are shown in FIG. 4. 40°–50° C. is regarded as the optimum temperature for the enzyme.

(7) Substrate specificity

Enzymatic activities of the enzyme on various substrates as shown in the Table 1 below are measured with the same procedures as the measurement of the enzyme activity by using 5 m mole of the substrate and 0.007 U of the enzyme. The results are shown in the Table 1 below.

TABLE 1

| Substrate | Relative activity (%) | Substrate | Relative activity (%) |
|---|---|---|---|
| L-Leucine | 100.0 | L-Histidine | 11.8 |
| L-Methionine | 93.6 | L-Cysteine | 6.4 |
| L-Phenylalanine | 70.0 | D-Phenylalanine | 0.0 |
| L-Arginine | 39.9 | L-Glycin | 0.0 |
| L-Lysine | 29.6 | L-Cysteine | 0.0 |
| L-Isoleucine | 29.1 | L-Serine | 0.0 |
| DL-Tryptophan | 27.1 | L-Aspartic acid | 0.0 |
| L-Tyrosine | 22.2 | L-Glutamic acid | 0.0 |
| DL-Isoleucine | 15.3 | D-Alanine | 0.0 |
| L-Alanine | 12.3 | | |

The enzyme of the present invention acts upon not only L-leucine but other various L-amino acids.

(8) Inhibition and Activation

The enzymatic activities of the enzyme are measured with the same procedures as the measurement of the enzyme activity using 0.01 U of the enzyme, and adding 1 mM of various metallic ions or other additives as shown in Table 2 below to the reaction solution. The results are shown in the Table 2 below. Cyano ion has a strong inhibiting effect on the enzyme and no ion is found to have an activating effect on the enzyme.

TABLE 2

| Additive | Relative activity (%) | Additive | Relative activity (%) |
|---|---|---|---|
| None | 100 | LiCl | 97.5 |
| NaN$_3$ | 100 | NH$_4$Cl | 97.1 |
| MnCl$_2$ | 97.1 | MgCl$_2$ | 99.2 |
| NaF | 97.9 | BaCl$_2$ | 97.1 |
| EDTA | 100 | CaCl$_2$ | 95.4 |
| KCN | 14.1 | ZnCl$_2$ | 94.2 |
| CoCl$_2$ | 50.6 | | |

(9) Isoelectric point pH 3.9

(10) Km value $1.7 \times 10^{-4}$ M (upon L-leucine)

(11) Molecular weight

Approximately 200,000; measured by gelfiltration using Sephacryl S-200.

From the above physiological characteristics, it is apparent that the enzyme of the present invention is L-amino acid oxidase.

The L-amino acid oxidase provided by the present invention is useful for quantitative analysis of amino acids, for clinical analysis wherein the amount of an amino acid derived from a synthetic substrate for measurement of peptidases such as leucine amino peptidase is determined, for the production α-keto acids useful for patients suffering from uremia, and the like.

The following non-limiting example is given by way of illustration only.

EXAMPLE 1

The Colletotrichum sp. M5073 (FERM-P No. 5441) was inoculated in each of two 500 ml flasks wherein 100 ml of culturing medium (pH 6.7, sterilized at 120° C. for 20 minutes) having a composition of maltose 1.0%, yeast extract 1.0%, NaCl of 0.5%, MgSO$_4$.7H$_2$O 0.05%, K$_2$HPO$_4$ 0.05%, rice bran 1.0% and defoaming agent 0.5% is placed, and incubated at 30° C. for 3 days with shaking to give seed cultures.

These two seed cultures were inoculated into 20 l of the same culturing medium as above in 30 l of a jar fermenter and cultivated at 30° C. for 3 days with stirring at 300 rpm and aeration of 20 l/min. Thereafter, the wet microorganism cells were isolated by centrifuging the medium for 10 minutes at 5,000 rpm. The isolated wet cells were suspended in 2 l of 10 mM Tris-HCl buffer solution (pH 7.5). The cells were destroyed with a destructor (brand name: DYNOMIL) and centrifuged at 15,000 rpm for 10 minutes to give 1.55 l of supernatant (2,700 U). This supernatant was subjected to 0.61 saturation ammonium sulfate fractional precipitation and centrifuged at 15,000 rpm for 10 minutes to give supernatant.

The supernatant was again subjected to 0.88 saturation ammonium sulfate fractional precipitation and centrifuged at 15,000 rpm for ten minutes to give precipitate. The precipitates were dissolved in 400 ml of 10 mM Tris-HCl buffer solution (pH 7.5) and warmed to 60° C. for 10 minutes. The resulted precipitates were removed therefrom by centrifugation (15,000 rpm, 10 minutes) to give 385 ml of supernatant. 456 ml of cold acetone was added to this supernatant. The resulted precipitates were recovered, and dissolved in 150 ml of 0.2 M Tris-HCl buffer solution (ph 7.5). The undissolved material was centrifugally removed therefrom to give 112 ml of supernatant. This liquid was dialyzed over night against 5 l of 10 mM Tris-HCl buffer solution (pH 7.5) with a cellulose acetate tube and then charged in a DEAE-cellulose column (4.0×30 cm) using 10 mM Tris-HCl buffer solution (pH 7.5), eluted using 0–0.5 M KCl with a linear concentration gradient, and the fractions which show activity were collected with about 0.4 M KCl. These active fractions were concentrated with an ultrafiltration membrane XM-50 (produced by Amicon), charged in a column (3.6×80 cm) packed with Sephacryl S-200, and eluted with 10 mM Tris-HCl buffer solution (pH 7.5). The eluent which emerged after passage of 558 ml of eluent was collected until the total eluent was 640 ml. The collected eluent was freeze-dried to give 152 mg (621 U) of powdery L-amino acid oxidase.

We claim:

1. A process for producing L-amino acid oxidase which comprises culturing in a culture medium a microorganism which produce L-amino acid oxidase and is a member of the genus Colletotrichum, and recovering L-amino acid oxidase from the cells cultured.

2. A process as claimed in claim 1 wherein the L-amino acid oxidase producing microorganism is Collectotrichum sp. M5073 having the deposition No. FERM-P No. 5441.

* * * * *